United States Patent [19]

Kawashima

[11] Patent Number: 4,731,224

[45] Date of Patent: Mar. 15, 1988

[54] DEODORIZER

[75] Inventor: Mikio Kawashima, Kashiwa, Japan

[73] Assignee: Hitachi Elevator Engineering and Service Co., Ltd., Tokyo, Japan

[21] Appl. No.: 778,964

[22] Filed: Sep. 23, 1985

[30] Foreign Application Priority Data

Dec. 14, 1984 [JP] Japan .................. 59-262903

[51] Int. Cl.$^4$ ..................... B01D 47/00; D01D 47/02
[52] U.S. Cl. ........................... 422/49; 422/122; 55/234; 55/240; 55/279; 55/351; 55/400; 55/481; 261/92
[58] Field of Search ............ 422/122, 4, 124, 49; 55/234, 279, 240, 351, 400, 481; 261/92, DIG. 17

[56] References Cited

U.S. PATENT DOCUMENTS

| | | | |
|---|---|---|---|
| 1,544,690 | 7/1925 | Shurtleff | 55/481 |
| 2,356,235 | 8/1944 | Fulcher | 261/92 |
| 3,328,941 | 7/1967 | Green | 55/351 |
| 3,902,877 | 9/1975 | Swaim | 55/279 |
| 4,102,656 | 7/1978 | Koritz | 422/124 |
| 4,304,230 | 12/1981 | Seufert | 55/234 |

Primary Examiner—David L. Lacey
Assistant Examiner—Floyd E. Bennett, Jr.
Attorney, Agent, or Firm—Oblon, Fisher, Spivak, McClelland & Maier

[57] ABSTRACT

A deodorizer is constructed of a casing defining an intake opening and a discharge opening, a blower provided in opposition to the intake opening, a filter provided in the flow passage of an air stream to be produced by the blower, and a reservoir for storing an odor-absorbing liquid therein. The blower, filter, and reservoir are all housed within the casing.

3 Claims, 4 Drawing Figures

DEODORIZER

BACKGROUND OF THE INVENTION (1) Field of the Invention

This invention relates to a deodorizer, and particularly to a deodorizer suitable for use in deodorizing relatively small spaces such as rooms.

(2) Description of the Prior Art

More and more attention has been paid to the improvement of the living environment in recent years. The primary concern has heretofore been directed to the toxicity of industrial waste from factories and the like to human. However, those giving unpleasant feeling have recently been being subjected to control. For example, offensive or unpleasant odor (hereinafter called "odor" for the sake of brevity) has been subjected to control. Its control has been carried out since 1974 in Tokyo, Japan.

As odor sources, there are many places such as kitchens and toilets in individual houses. Thus, a variety of deodorizers and deodorants have been proposed to deodorize rooms. However, thresholds of an average man or woman, in other words, concentrations at which such an average man or woman begins to recognize the presence of their corresponding odors are extremely low, i.e., 0.59 ppm for ammonia and 0.00065 ppm for methylmercaptan. Furthermore, there are many types of odors. It was hence unable to achieve sufficient deodorizing effects by these deodorizers or deodorants.

For example, activated carbon which is used most extensively as a deodorizer has selectivity in absorption of odors. This drawback can also be seen with refined vegetable oils, amino-acid base deodorants, chlorophyll-base deodorants and the like. Deodorizers in which odor components are oxidized with ozone produced by silent discharges have also been known as disclosed in Japanese Patent Laid-Open No. 12732/1984. Although these deodorizers exhibited deodorizing and sterilizing effects without need for replacement of deodorant, their effectiveness were limited to basic odors such as ammonia, and they were ineffective against neutral and acidic odors.

OBJECT OF THE INVENTION

An object of this invention is to provide a deodorizer which can bring about high deodorizing effects against various odors.

SUMMARY OF THE INVENTION

It has surprisingly been found that the above object of this invention can be achieved if forced deodorization is effected by combining a filter which is wet with an odor-absorbing liquid with a blower.

In one aspect of this invention, there is thus provided a deodorizer which comprises:
- a casing defining an intake opening and a discharge opening;
- a blower provided in opposition to the intake opening;
- a filter provided in the flow passage of an air stream to be produced by the blower;
- means for supplying an odor-absorbing liquid to the filter; and
- a reservoir for storing the odor-absorbing liquid therein, said blower, filter, means and reservoir being all housed within the casing.

The deodorizer of this invention shows highly efficient deodorizing effects against various odors.

The above and other objects, features and advantages of the present invention will become apparent from the following description and the appended claims, taken in conjunction with the accompanying drawings.

DETAILED DESCRIPTION OF THE INVENTION AND PREFERRED EMBODIMENTS

Figure 1:
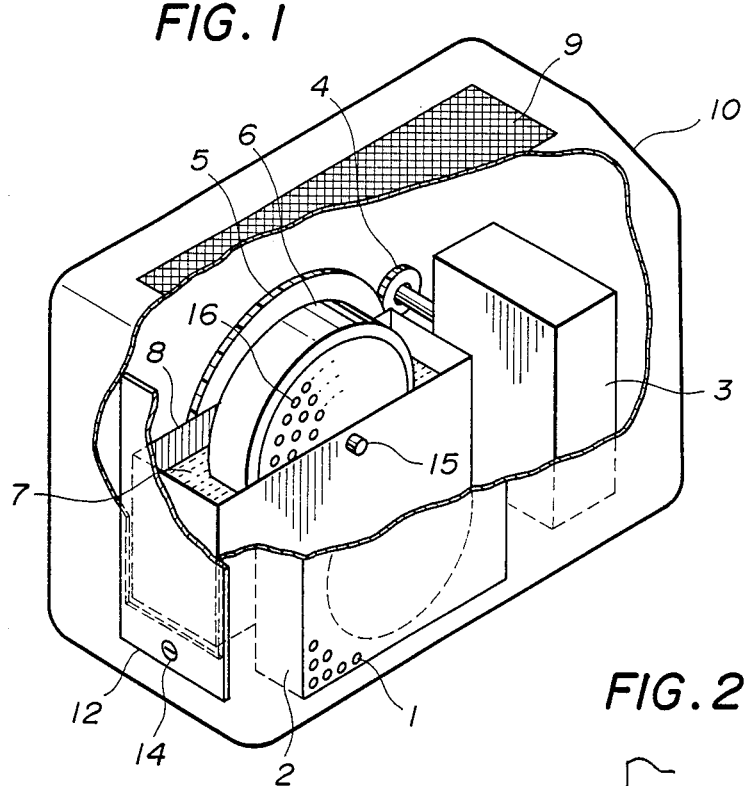
FIG. 1 is a partially cut-away perspective view of a deodorizer according to the first embodiment of this invention.

Referring first to FIG. 1, all elements of structure of the deodorizer according to the first embodiment of this invention are housed within a casing 10. Through the front wall and upper wall of the casing 10, grid- or net-like intake opening 1 and discharge opening 9 are formed respectively. A thin blower 2 (for example, a fan) is provided on the inner wall of the casing 10 at a position corresponding to the intake opening 1. A reservoir 8 is arranged in parallel to the blower 2.

Figure 2:
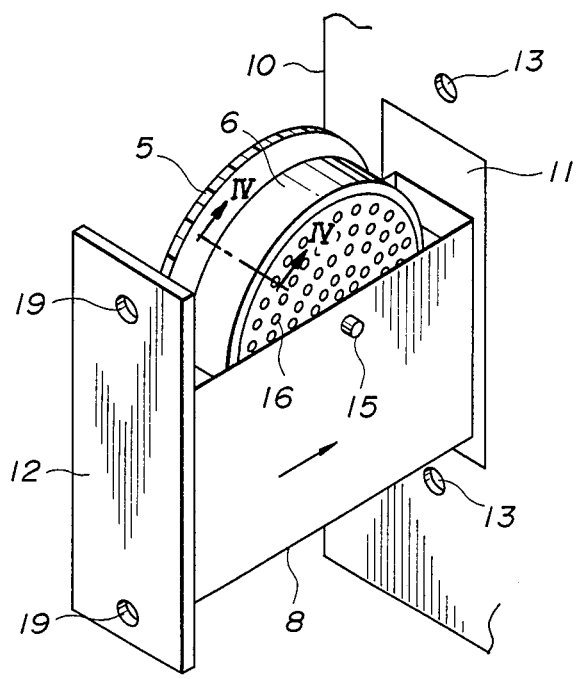
FIG. 2 is a perspective view showing how a reservoir is taken out of the deodorizer of FIG. 1.

As illustrated in FIG. 2, the reservoir 8 is pushed into the casing 10 through an opening 11 formed through a side wall of the casing 10. The reservoir 8 is equipped with a side plate 12 having dimensions greater than the opening 11. A pair of holes 19 are formed in the side plate 12. The reservoir 8 is held in place by causing screws 14 to extend through the holes 19 into corresponding internally-threaded holes 13 formed through the casing 10.

An odor-absorbing liquid 7 is stored in the reservoir 8. A shaft 15 of a filter 6, approximately the lower half of which is immersed in the odor-absorbing liquid 7, is supported rotatably on the reservoir 8. The filter 6 is composed of a flattened drum-like container 20 made of a plastic material and non-hygroscopic fibers 21 such as glass wool filled within the container. The front and rear walls of the container 20, which lie substantially in parallel with the blower 2, contain many through-holes 16 respectively. When the filter 6 is rotated, the odor-absorbing liquid 7 is allowed to enter the filter 6 through the lower through-holes 16. At the same time, the air which has been blown to the filter 6 by the blower 2 is allowed to flow into the filter 6 through the upper through-holes 16 in the front wall of the container. The air is brought into contact with the odor-absorbing liquid 7 and is then allowed to leave the filter 6 through the through-holes 16 in the rear wall of the container 20. The air is finally discharged through the discharge opening 9. Owing to this flow of the air, the odor components are dissolved in the odor-absorbing liquid 7.

The rotation of the filter 6 will next be described. Behind the reservoir 8, a toothed wheel 5 is fixed on the shaft 15. Therefore, the toothed wheel 5 is designed to rotate together with the filter 6. A gear 4 which is arranged in meshing engagement with the toothed wheel 5 is connected to a slow-speed motor 3. The slow-speed motor 3 is secured to the casing 10 at a position deeper than the inner end wall of the inserted reservoir 8. The rotation speed of the filter 6 is determined by the revolution number of the slow-speed motor 3 and the gear ratio between the gear 4 and the toothed wheel 5.

Other connecting means such as a belt or the like may also be used as means for connecting the slow-speed motor 3 with the filter 6. Use of the gear 4 and the toothed wheel 5 however, permits easy removal of the reservoir 8 for inspection and maintenance as depicted in FIG. 2 as well as easy insertion of the reservoir 8. By providing rotary means such as the slow-speed motor 3 at the deepest position in the opening 11 of the casing 10 and arranging the blower 2 and the reservoir 8 side by side in the vicinity of the opening 11, it is possible not only to obtain the above-mentioned effects, but also to make the overall dimensions of the deodorizer smaller.

The deodorizing effects of a deodorizer of the above-mentioned construction vary depending what is used as the odor-absorbing liquid 7 in the reservoir 8. In order to demonstrate clearly the difference in effectiveness between the deodorizer according to the first embodiment of this invention and a conventional deodorizer or deodorant, the performance of the deodorizer according to the first embodiment of this invention was compared using water (the effectiveness of which is the lowest) as the odor-absorbing liquid 7.

Ammonia was charged in a closed space of 100 liters to about 200 ppm. The concentration of ammonia was measured by a Kitagawa's detection tube while operating the deodorizer according to the first embodiment of this invention and a conventional deodorizer separately at an airflow rate of 1 m³/min. Incidentally, the dimensional specification of the deodorizer shown in FIG. 1 is as follows:

Effective dimensions of the filter 6:
  Radius: 80 mm; Thickness: 20 mm.
Outer dimensions of the casing 10:
  Thickness: 150 mm; width: 400 mm;
  Height: 300 mm.
Dimensions of the reservoir 8:
  Thickness: 50 mm; Width: 180 mm;
  Height: 95 mm.

A similar experiment was also conducted by charging hydrogen chloride in the closed space. As the conventional deodorizer, a deodorizer having a size approximately equal to the area of rotation of the blower 2 in the deodorizer shown in FIG. 1 and packed with activated coconut husk carbon was used.

As readily envisaged from the following table which shows results of the experiments, the deodorizer according to the first embodiment of this invention (which is indicated by "B" in the table) had superior deodorizing effects to the conventional deodorizer (which is indicated by "A" in the table) and exhibited substantially the same effects against various odors, even when water was used as an odor-absorbing liquid.

| | | | | | (unit: ppm) |
|---|---|---|---|---|---|
| | | Time passed (min.) | | | |
| | 0 | 10 | 15 | 20 | 30 |
| A Ammonia | 210 | 140 | 100 | 60 | 30 |
| Hydrogen chloride | 200 | 180 | 160 | 150 | 140 |
| B Ammonia | 205 | 30 | 10 | 0 | 0 |

-continued

| | | | | | (unit: ppm) |
|---|---|---|---|---|---|
| | | Time passed (min.) | | | |
| | 0 | 10 | 15 | 20 | 30 |
| Hydrogen chloride | 200 | 20 | 5 | 0 | 0 |

In the above experiments, water was used as the odor-absorbing liquid 7. The deodorizing effects can be improved further if a liquid with an ampholytic surfactant mixed therein is used as the odor-absorbing liquid 7.

In the deodorizer depicted in FIG. 1, the air stream which passes through the filter 6 is formed by the blower 2, and the filter 6 is rotated to supply the odor-absorbing liquid 7 to the filter 6. Alternatively, the filter may be fixed and instead, the odor-absorbing liquid may be caused to flow downwardly from a point above the fixed filter. It is necessary for the deodorizer of this invention to have means for supplying an odor-absorbing liquid to the flow passage of air stream passing through its filter, irrespective of the construction of the filter. As the fibers 21, a material which does not absorb liquid (such as glass wool) may be used as in the above embodiment. Alternatively, a material which absorbs liquid can also be used. The replacement of the odor-absorbing liquid 7 is easy especially when the former material is used. In the practice of this invention, it is also recommendable to design the flow passage in such a way that the air stream is allowed to pass through the filter 6 so as to enhance the efficiency of the blower 2.

Figure 3:
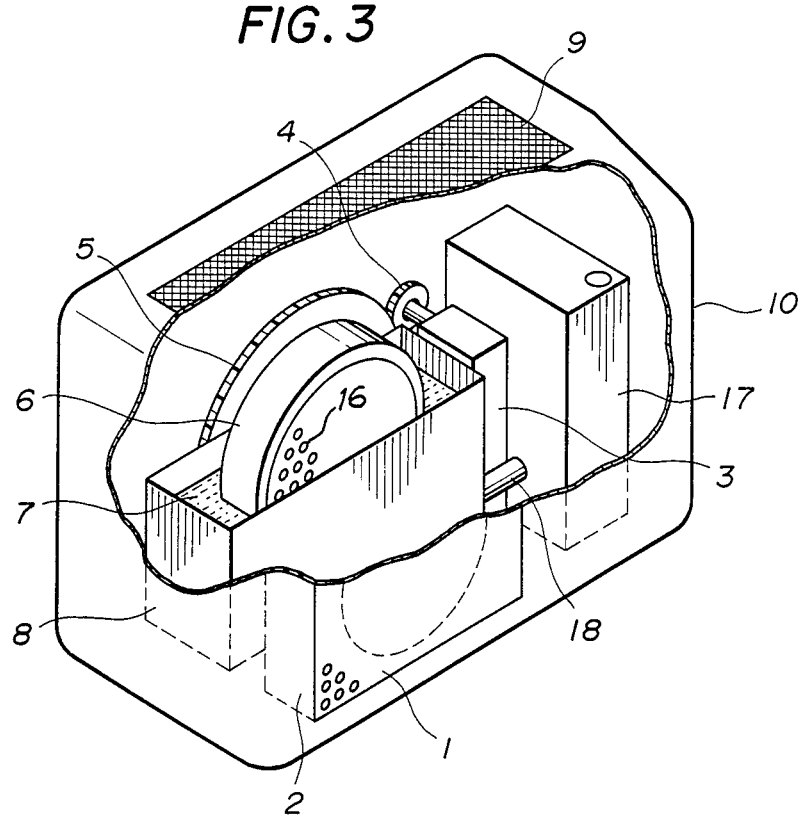
FIG. 3 is a partially cut-away perspective view of a deodorizer according to the second embodiment of this invention.
Figure 4:
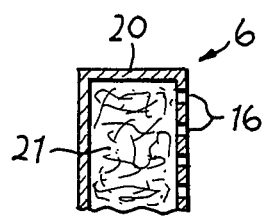
FIG. 4 is a sectional view along the plane IV—IV in FIG. 2.

The second embodiment of this invention is now described with reference to FIG. 3.

In the second embodiment, the casing 10 houses a tank 17 which is adapted to store the odor-absorbing liquid. The tank 17 is connected to the reservoir 8 by way of a connector pipe 18 and an unillustrated pump. Through the connector pipe 18, the odor-absorbing liquid can be fed from the tank 17 to the reservoir 8. The remaining fundamental structures may for example be equal to the corresponding structures in the first embodiment.

In the second embodiment having the above-described structure, the odor-absorbing liquid can be continuously fed from the tank 17 to the reservoir 8 and the filter 6 through the connector pipe 18 even when the odor-absorbing liquid 7 is consumed in a large volume at the filter 6 owing to the air blown from the blower 2 to the filter 6. It is therefore possible to set the effective operation time sufficiently long for the deodorizer, whereby higher deodorizing effects are assured.

Having now fully described the invention, it will be apparent to one of ordinary skill in the art that many changes or modifications can be made thereto without departing from the spirit or scope of the invention as set forth herein.

I claim:
1. A deodorizer comprising:
  (a) a casing containing an air intake opening, an air discharge opening, and a reservoir inserting opening;
  (b) a blower disposed in said casing in opposition to said air intake opening so as to create an air stream from said air intake opening to said air discharge opening;
  (c) a reservoir which, in use, contains an aqueous odor-absorbing liquid;

(d) a filter composed of a flattened drum-like container having through-holes therethrough and containing non-hygroscopic fibers, said filter being rotatably mounted in said reservoir such that, in use, an upper portion of said filter is in the air stream produced by said blower and a lower portion of said filter extends into said reservoir, said reservoir and said filter comprising an assembly detachably operatively mounted in said casing;

(e) a motor disposed in said casing and detachably operatively connected to said filter, said motor serving, when operatively connected to said filter, to rotate said filter about an at least substantially horizontal axis automatically and continuously; and (f) a plate integral with said reservoir and positioned so as to close said reservoir inserting opening when said assembly is detachably operatively mounted in said casing.

2. A deodorizer as recited in claim 1 wherein said non-hygroscopic fibers are glass wool.

3. A deodorizer as recited in claim 1 and further comprising means for detachably securing said plate to said casing.

* * * * *